(12) United States Patent
Stamm et al.

(10) Patent No.: US 6,891,045 B1
(45) Date of Patent: May 10, 2005

(54) METHOD FOR PRODUCING CARBONYLDIIMIDAZOLE

(75) Inventors: Armin Stamm, Mainz; Jochem Henkelmann, Mannheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/719,354

(22) PCT Filed: Jun. 14, 1999

(86) PCT No.: PCT/EP99/04092

§ 371 (c)(1),
(2), (4) Date: Dec. 12, 2000

(87) PCT Pub. No.: WO00/14072

PCT Pub. Date: Mar. 16, 2000

(30) Foreign Application Priority Data

Jun. 17, 1998 (DE) .......................................... 198 26 936

(51) Int. Cl.$^7$ .............................................. C07D 403/04
(52) U.S. Cl. ................................................... 548/313.7
(58) Field of Search ..................................... 548/313.7

(56) References Cited

U.S. PATENT DOCUMENTS 4,965,366 A 10/1990 Novy .......................... 548/110

FOREIGN PATENT DOCUMENTS

EP 0 692 476 1/1996

*Primary Examiner*—Joseph K. McKane
*Assistant Examiner*—Joseph Murray
(74) *Attorney, Agent, or Firm*—Keil & Weinkauf

(57) ABSTRACT

In a process for preparing carbonyldiimidazole from imidazole and phosgene in an inert solvent, the imidazole hydrochloride which results as coupled product is removed as melt from the resulting reaction mixture by phase separation.

5 Claims, No Drawings

METHOD FOR PRODUCING CARBONYLDIIMIDAZOLE

The present invention relates to an improved process for preparing carbonyldiimidazole from imidazole and phosgene by simplified removal and recycling of the imidazole from its hydrochloride coupled product.

Carbonyldiimidazole (CDI) is a reagent frequently used to introduce carbonyl groups, for example for preparing carbonates, ureas or urethanes, or for activating unreactive reactants in ester or amide synthesis (Angew. Chem. 74 (1962), 407).

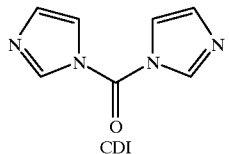

CDI

Two ways of preparing carbonyldiimidazole are known in principle. Chem. Ber. 93 (1960), 2804 and U.S. Pat. No. 4,965,366 describe a two-stage process in which initially imidazole is reacted with trimethylsilyl chloride to give 1-trimethylsilylimidazole and the latter is then reacted with phosgene to give CDI in accordance with the following scheme.

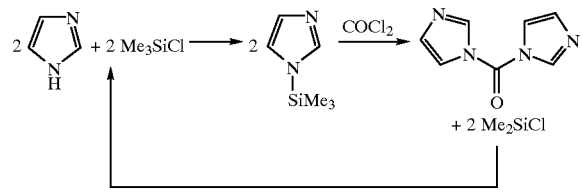

Although the trimethylsilyl chloride can be recycled for reuse, this synthetic route takes a considerable time to implement and thus results in a poor space-time yield of the required product. In addition, the manipulation of the hydrolysis-sensitive trimethylsilyl chloride makes additional demands on the reaction apparatus.

The more elegant route for preparing CDI is the direct phosgenation of imidazole which was originated by Staab et al. and described in various publications (Liebigs Ann. Chem. 609 (1957), 75; Chem. Ber. 96 (1963), 3374; Org. Synth. Coll. Vol V (1973), 201). Although this results in two moles of imidazole hydrochloride as coupled product per mole of CDI, the former can be converted back into imidazole by basic workup and be returned to the phosgenation:

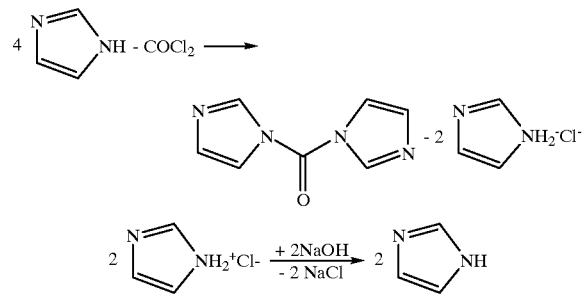

EP-A 0 692 476 extends the synthetic route described in the preceding references merely by a method for dehydrating the solvent. However, a considerable difficulty of the original methods persists. The imidazole hydrochloride also formed as coupled product must be removed from the CDI-containing reaction solution at high temperatures (80 to 100° C.) by a filtration with exclusion of moisture. Great technical complexity is necessary in order to maintain a sufficiently high product quality because the CDI is extremely hydrolysis-sensitive.

It is an object of the present invention to improve the original process to avoid the elaborate filtration with exclusion of moisture. We have found that this object is achieved by a process for preparing carbonyldiimidazole from imidazole and phosgene in an inert solvent, in which the imidazole hydrochloride coupled product is removed as melt from the resulting reaction mixture by phase separation. The imidazole hydrochloride formed is removed as melt preferably at a temperature above 100° C., preferably at 110 to 130° C. Since the imidazole hydrochloride melt results as the lower phase, it can be removed simply by discharging the lower phase after the phase separation has taken place. Solvents which can be employed in principle are all those boiling above 130° C. and inert to phosgene, but preferably chlorobenzene and xylene; xylene is particularly preferably employed as solvent.

The temperature necessary for melting the imidazole hydrochloride which results as a solid under the reaction conditions is, surprisingly, distinctly lower than the melting point stated in the literature for the pure hydrochloride of 158 to 161° C. Without being committed to one theory, it is assumed that there is either formation of a eutectic mixture of imidazole hydrochloride with CDI, which dissolves in the molten hydrochloride in accordance with the Nernst distribution law, or formation of a ternary mixture of CDI, imidazole hydrochloride and the solvent, which lowers the melting point of the pure hydrochloride.

The melting point of the hydrochloride phase differs from experiment to experiment and evidently depends on the solvent, on the composition of the reaction mixture, in particular the amount of phosgene added, and on the concentration of the individual components.

The CDI present in the solution crystallizes in pure form on cooling the xylene solution and can be isolated in high purity by filtration with suction at 0 to 50° C., preferably at room temperature, under dry inert gas, without further washing.

The imidazole hydrochloride solidifies on cooling. It still contains some dissolved CDI which, on hydrolysis with water, reacts to form $CO_2$ and imidazole. Imidazole can be liberated again from the imidazole hydrochloride by adding a solvent which is virtually immiscible with water, for example a water-insoluble carboxylic ester, preferably ethyl acetate, or an aromatic hydrocarbon, preferably the solvent which can be used for the process described above, and neutralizing with sodium hydroxide solution or another strong base to a pH between 11 and 12, and can be transferred almost quantitatively into the organic phase. The dissolved imidazole is then used again in the process described above. The water dissolved in the organic solvent is removed azeotropically from the precursor mixture using a water trap.

The process is illustrated in detail by the following examples.

EXAMPLE 1

The reaction is carried out in a 2l jacketed reactor with gas inlet, stirrer and fitted condensing system. 136 g (2 mol) of imidazole are suspended in 1010 g of xylene (isomer mixture) in the reactor. On heating to the reflux temperature, the imidazole dissolves completely at about 65° C. A total of 10 g of xylene is taken off under reflux to remove water in a water trap. The temperature of the precursor solution is then lowered again to 66° C. Over the course of 30 minutes, a total of 51 g of phosgene (0.51 mol) is passed in, during which the reaction temperature rises to a maximum of 76° C. After a reaction time of about 20 minutes, two phases form. The upper one is clear and colorless. The lower phase, which contains the imidazole hydrochloride formed, does not separate out in the form of colorless crystals but forms a viscous, lumpy paste which melts completely at 108° C. (internal temperature) after a further reaction time of 1 h and an increase in the external temperature to 130° C.

The molten phase is discharged at 110° C. and solidifies on cooling. 91 g remain after drying in vacuo. The carbonyldiimidazole separates out as colorless needles from the cooling reaction solution. The crystals are filtered off with suction under dry nitrogen and dried in vacuo. 36 g of carbonyldiimidazole with a melting point of 110 to 112° C. and an elemental analysis agreeing with theory are obtained.

A further 5.5 g of carbonyldiimidazole can be obtained from the mother liquor by concentration.

EXAMPLE 2

Example 1 is repeated with the same batch size. Once again the imidazole dissolves completely at 65° C. Over the course of 30 minutes, a total of 52 g of phosgene is passed in at a temperature of 65 to 77° C. After 20 minutes, imidazole hydrochloride separates out as in Example 1 as a viscous brown paste which does not melt completely until 120° C. The lower phase is discharged at 120° C.; cooling and drying in vacuo result in 128 g of a dark brown solid.

The carbonyldiimidazole once again separates out the reaction solution in the form of colorless crystalline needles. Filtration with suction under dry nitrogen and drying in vacuo results in 40.5 g of colorless crystals of melting point 110 to 112° C. A further 8 g of carbonyldiimidazole are obtained from the mother liquor by concentration.

EXAMPLE 3

Imidazole Recycling

The imidazole hydrochloride fractions from Examples 1 and 2 are combined and dissolved in about 250 ml of water. Much evolution of $CO_2$ is observed during this, caused by hydrolysis of the carbonyldiimidazole dissolved in the hydrochloride. After the gas evolution has ceased, the dark brown solution is covered with about 1 liter of ethyl acetate. The mixture initially has a pH of 6.9. 40% strength aqueous NaOH solution is metered in while stirring until the pH remains stable at a constant value of 12 for a lengthy period. The temperature rises during the addition to a maximum of 44° C. Some salt crystallizes out of the aqueous phase and is dissolved by adding a little water.

The aqueous phase is separated off and back-extracted four times with 50 ml of ethyl acetate each time. The combined ethyl acetate phases are distilled to remove the solvent at 42° C. under 190 mbar. Drying results in 164 g of recycled imidazole.

EXAMPLE 4

Reuse of the Recycled Imidazole 164 g of recycled imidazole from Example 3 are suspended in 1300 g of xylene. A xylene/water azeotrope is removed until the xylene collecting in the water trap no longer shows any cloudiness. A total of 60 g of phosgene is passed in at 60 to 73° C. over the course of 35 minutes. Two phases form after 15 minutes. After about 1 h, the lower phase which contains the hydrochloride is deep black. It melts at 120° C. and is discharged at 120° C.

Colorless needles of carbonyldiimidazole crystallize out of the upper phase on cooling and, after filtration with suction under dry nitrogen and drying in vacuo, have a melting point of 110° C. 41 g of product are isolated.

A further 14 g of carbonyldiimidazole are obtained from the mother liquor by concentration.

We claim:

1. A process for preparing carbonyldiimidazole from imidazole and phosgene at a temperature in the range from 60 to 80° C. in a substituted aromatic hydrocarbon as solvent, in an inert solvent, in which the imidazole hydrochloride coupled product is removed as melt from the resulting reaction mixture by phase separation at a temperature above 100° C., wherein ortho-, meta- or para-xylene or a mixture composed of these isomers in any ratio or chlorobenzene is used as substituted aromatic hydrocarbon.

2. A process as claimed in claim 1, wherein the imidazole hydrochloride is melted after the reaction by increasing the temperature to 100 to 130° C. and is then removed by phase separation.

3. A process as claimed in claim 1, wherein the imidazole hydrochloride removed as melt is hydrolyzed with water, then neutralized with the aqueous solution of a strong base by adjusting to a pH of from 11 to 12, and extracted from the aqueous phase using an organic solvent.

4. A process as claimed in claim 3, wherein a water-insoluble carboxylic ester is used as organic solvent for the extraction.

5. A process as claimed in claim 3, wherein the imidazole solution recovered by extraction is dehydrated by azeotropic removal of the water present in the solution and is returned to the phosgenation.

* * * * *